United States Patent [19]
Rinehart et al.

[11] Patent Number: 5,256,663
[45] Date of Patent: Oct. 26, 1993

[54] COMPOSITIONS COMPRISING ECTEINASCIDINS AND A METHOD OF TREATING HERPES SIMPLEX VIRUS INFECTIONS THEREWITH

[75] Inventors: Kenneth Rinehart; Sakai Ryuichi, both of Urbana, Ill.; Tom G. Holt, Westfield, N.J.

[73] Assignee: The Board of Trustees of the University of Illinois, Champaign, Ill.

[21] Appl. No.: 838,149

[22] Filed: Feb. 18, 1992

Related U.S. Application Data

[63] Continuation-in-part of Ser. No. 620,427, Nov. 30, 1990, Pat. No. 5,149,804, and a continuation-in-part of Ser. No. 548,060, Jul. 5, 1990, Pat. No. 5,089,273, which is a continuation-in-part of Ser. No. 278,629, Dec. 1, 1988, abandoned, which is a continuation of Ser. No. 1,226, Jun. 1, 1987, which is a continuation-in-part of Ser. No. 6,395, Jan. 23, 1987, abandoned, which is a continuation-in-part of Ser. No. 898,906, Aug. 21, 1986, abandoned, which is a continuation-in-part of Ser. No. 872,189, Jun. 9, 1986, abandoned.

[51] Int. Cl.$^5$ ............................................. A61K 31/495
[52] U.S. Cl. .................................... 514/250; 514/934
[58] Field of Search ......................................... 514/250

[56] References Cited

FOREIGN PATENT DOCUMENTS 9225189 12/1984 Japan.

Primary Examiner—Frederick E. Waddell
Assistant Examiner—Russell Travers
Attorney, Agent, or Firm—Ernest V. Linek

[57] ABSTRACT

The present invention relates to pharmaceutical compositions comprising matter extracted from the well-known and readily available tropical marine invertebrate, *Ecteinascidia turbinata*, and designated herein as ecteinascidins, and to the use of such compositions as antibacterial, anti-viral, and/or antitumor agents in mammals.

10 Claims, 4 Drawing Sheets

FIG. I

COMPOSITIONS COMPRISING ECTEINASCIDINS AND A METHOD OF TREATING HERPES SIMPLEX VIRUS INFECTIONS THEREWITH

CROSS-REFERENCE TO RELATED APPLICATIONS

This application is a continuation-in-part of U.S. Ser. No. 07/620,427, filed Nov. 30, 1990, now U.S. Pat. No. 5,149,804 and U.S. Ser. No. 07/548,060, filed Jul. 5, 1990, issued on Feb. 18, 1992, as U.S. Pat. No. 5,089,273, which is a continuation-in-part of U.S. Ser. No. 07/278,629, filed Dec. 1, 1988, now abandoned, which is a continuation of U.S. Pat. No. 87/01226 filed Jun. 1, 1987, which is a continuation-in-part of U.S. Ser. No. 006,395, filed Jan. 23, 1987, now abandoned, which is a continuation-in-part of U.S. Ser. No. 898,906, filed Aug. 21, 1986, now abandoned, which is a continuation-in-part of U.S. Ser. No. 872,189, filed Jun. 9, 1986, now abandoned. The disclosures of these applications are hereby incorporated herein by reference.

FIELD OF THE INVENTION

The present invention relates to novel compositions of matter. More particularly, the present invention relates to novel antibacterial agents designated herein as ecteinascidins 729, 743, 745, 759A, 759B and 770. These compounds are extracted from the marine tunicate *Ecteinascidia turbinata*, which is a well-known and readily available tropical marine invertebrate. Biological activity has been assigned previously to extracts of *E. turbinata;* see, for example, M. M. Sigel et al., "Anticellular and Antitumor Activity of Extracts from Tropical Marine Invertebrates," in Food-Drugs from Sea Proceedings (1969), Youngken, H.W., Jr., Ed., Marine Technology Society, Washington, D.C., 1970, pp. 281-294; Lichter, W. et al., "Biological Activities Exerted by Extracts of *Ecteinascidia turbinate,*" in Food-Drugs from the Sea Proceedings (1972), Worthen, L.R., Ed., Marine Technology Society: Washington D.C., 1973, pp. 117-127; Lichter, W., et al., "Inhibition of DNA Synthesis by *Ecteinascidia turbinate* Extracts (ETE)," in Food-Drugs from the Sea Proceedings, 1974, Webber, H.H., Ruggieri, G.D., Eds., Marine Technology Society: Washington, D.C., 1976, pp. 395-401; and Lichter, W. et al., "Immunomodulation by Extracts of *Ecteinascidia turbinate,*" in Drugs and Food From the Sea, Kaul, P.N., Sindermann, C.J., Eds., The University of Oklahoma, Norman, Okla., 1978, pp. 137-144.

SUMMARY OF THE INVENTION

The present invention particularly provides details regarding the ecteinascidins, particularly their structures and biological activity, as well as certain pharmaceutical compositions containing the active ecteinascidins.

The ecteinascidins (Et's) exhibit antimicrobial activity against Gram-positive bacteria and strong cytotoxicity against the L1210 murine leukemia cell line. Also Et's 722 (Compound 2) and 729 (Compound 3) exhibit potent in vivo activities against several tumor models in mice. The in vitro L1210 murine leukemia assay showed that Compound 3 was the most potent of all, and that Compound 1 was the least active by an order of magnitude. Et 743 (Compound 3) and Et 722 (Compound 2) showed intermediate activity. These compounds, except for Compound 1, which showed the steepest curve, followed similar dose-response curves (see FIG. 4). Et 736 (Compound 1) and Et 722 (Compound 2) inhibited the growth of *M. luteus* with inhibition zones of about 12 mm at 450 and 300 ng/disc, respectively in the paper disc diffusion assay, while Et 743 (Compound 4) and Et 729 (Compound 3) gave the same size zone at 100 and 140 ng/disc, respectively.

In vivo activities of Compounds 2 and 3 against P388 lymphoma, B16 melanoma, and Lewis lung carcinoma in mice, showed that Compound 3 required a lower does than Compound 2, and was more active in the solid tumor assays (B16 and Lewis lung). Interestingly, Compound 2 showed a higher T/C in the leukemia model than did Compound 3. Compound 3 showed excellent activities not only against B-16 melanoma but also Lewis lung carcinoma in this assay.

The antiproliferative activity of the Et's was measured by counting incorporation of [$^3$H]thymidine into the cells. Cell viability of non-stimulated cells (indicating general cytotoxicity) was assessed by MTT dye reduction. All of the Et's tested (Compounds 1-4) showed strong antiproliferative activity against the concanavalin A-stimulated spleen cells at $IC_{50}$'s of 2-4 ng/ml in which more than 90% of the cells were viable.

The Et's were also shown to suppress cell-mediated response of mouse spleen cells in vitro. An anti-mitogenesis assay was carried out using concanavalin A-stimulated mouse spleen cells which reveal the antiproliferative action of the compounds against activated T-cells. All Et's tested (Compounds 1-4) showed strong antiproliferative activity against activated T-cells.

All Et's tested (Compounds 1-4) showed strong antiproliferative activity against concanavalin A-stimulated murine spleen cells at $IC_{50}$'s of 3.6, 3.5, 1.9 and 2.7 ng/ml, respectively. At these concentrations cell viabilities are 97, 91, 88 and 89%, respectively. The Et 743 series were more active than the Et 736 series, but cell viability at $IC_{50}$ in the Et 736 series was higher than that of the Et 743 series. The relative potencies ($ED_{50}$ cytotoxicity/$IC_{50}$ antiproliferative activity) was highest (11.2) in Et 736 (Compound 1), while others showed values around 7 to 8, indicating Compound I has more selective antiproliferative activity than the other Et's tested.

DETAILED DESCRIPTION OF THE PREFERRED EMBODIMENTS

The organism from which the ecteinascidins were extracted is a marine colonial tunicate identified as *Ecteinascidia turbinate* by Dr. Françoise Lafargue, Université de Paris VI, Laboratoire Arago, Banyuls-sur-Mer, France. *E. turbinata* belongs to the family Perophoridae, suborder Phlebobrachia, order Enterogona, class Ascidiacea, subphylum Tunicata, phylum Chordata. Detailed descriptions of this readily available organism can be found in the following references, the disclosures of which, to the extent necessary, are hereby incorporated herein by reference:

1. W.G. VanName, "The Ascidians of the Bermuda Islands", *Trans. Conn. Acad. Arts Sci.*, 11, 325-412

(1902). See pages 338-339 for a description of *E. turbinata*.

2. W.G. VanName, "The North and South American Ascidians", *Bull. Amer. Museum Nat. Hist.*, 84, 1-476 (1945). See plate 20, text FIGS. 82A, 85, 86, and pages 169-171 for a complete description of *E. turbinata* and a comprehensive list of previous references.

3. H.H. Plough, "Sea Squirts of the Atlantic Continental Shelf from Maine to Texas", Johns Hopkins University Press, 1978, Baltimore, Md. See text figures 13, 30e, and pages 21-22, 54, and 68 for descriptions of *E. turbinata*.

*E. turbinata* is common and widely distributed in the Caribbean. It is conspicuous on account of the large size and often bright orange color of the colonies. A colony consists of a dense cluster of elongated, club-shaped zooids, which are connected at their tapered bases by a network of stolons that adheres to the surface of the object on which the colony grows. Colonies are found in shallow water (0-20 feet) growing on mangrove roots, sponges, rocks, shells, turtle grass, bridge pilings, bottom sand, stone, or the like. The animals are easily collected by wading, snorkeling, or SCUBA techniques.

Figure 1:
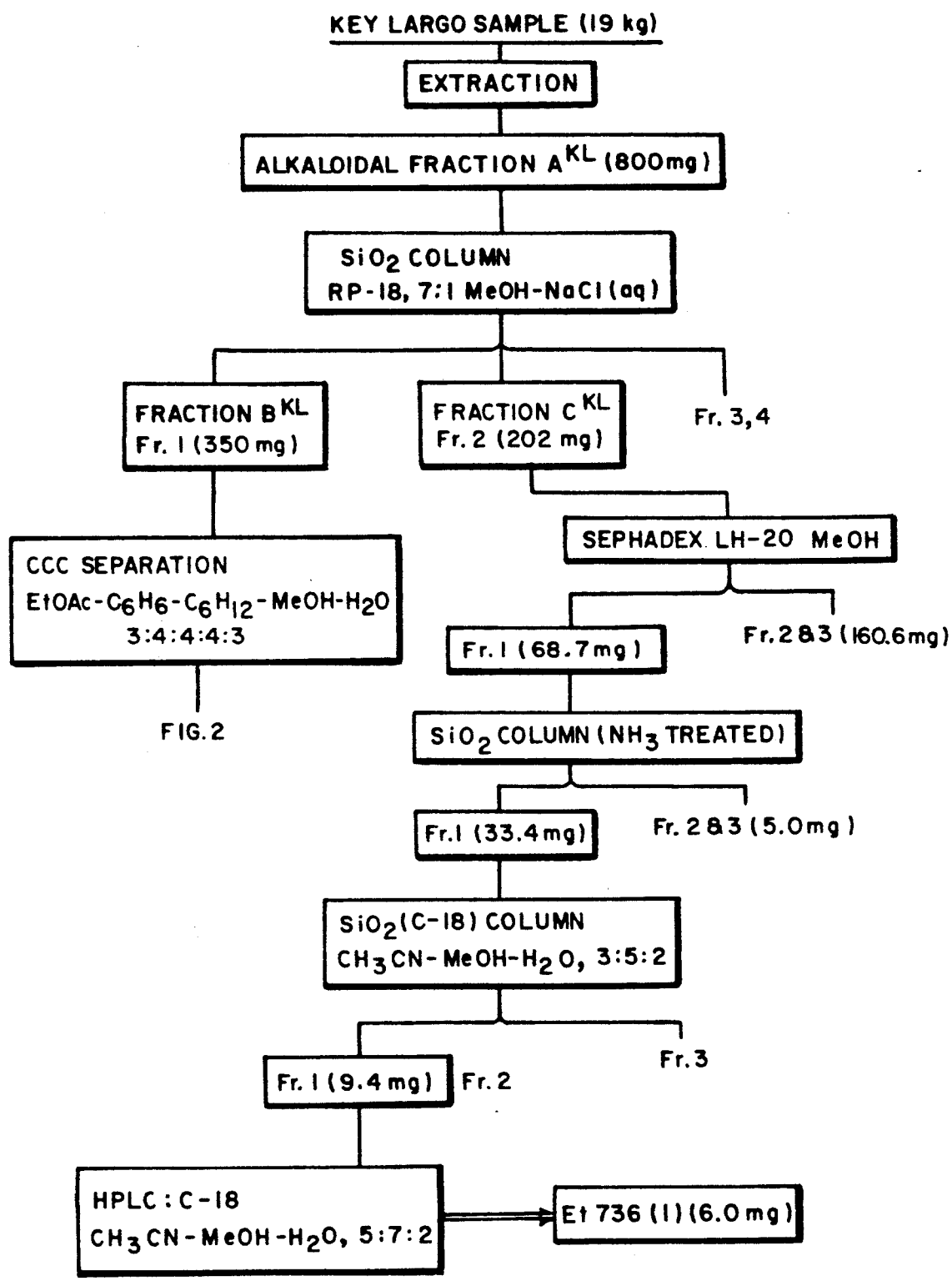
FIGS. 1, 2, and 3 illustrate the general scheme employed in the isolation of the various ecteinascidins (Et's) discussed herein.
Figure 2:
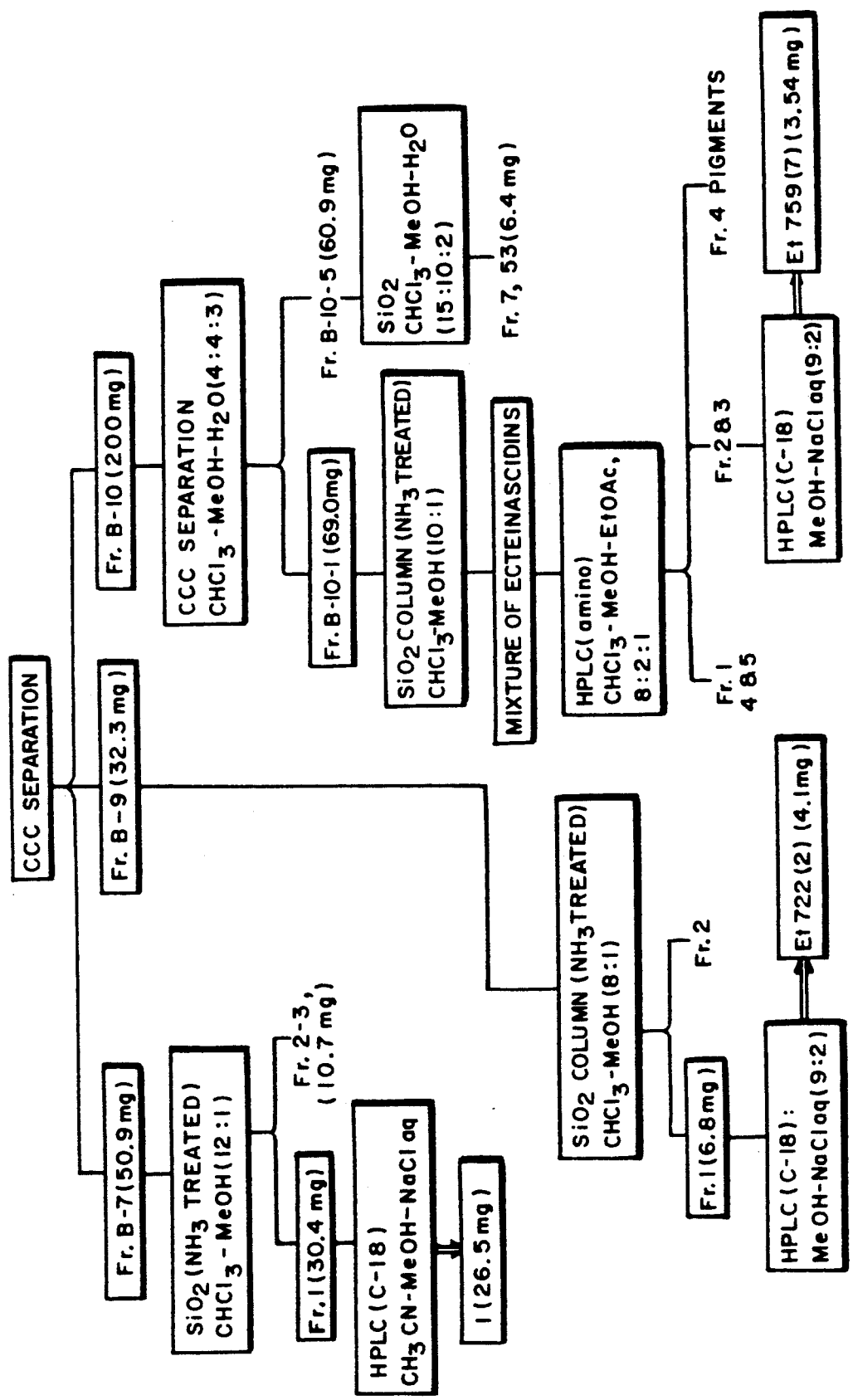

Ecteinascidins 736 (Compound 1), 722 (Compound 2), 729 (Compound 3), 743 (Compound 4), and 759B (Compound 6) were isolated from tunicate samples obtained at Key Largo, Fla. The sample collected at Key Largo (10 kg) was extracted and processed using previously employed procedures (see, FIG. 1). The alkaloid-rich fraction designated as "Fraction $A^{KL}$"(800 mg, FIG. 1) was separated on a reversed-phase silica gel gravity column to give four fractions. FABMS of each fraction showed that the first and the second fractions (Fractions $B^{KL}$ and $C^{KL}$) contained ecteinascidins. Fraction $B^{KL}$ was separated by CCC into 10 fractions (B-1 to B-10) and each fraction was examined by FABMS (see, Table 1).

TABLE 1

| CCC Separation and FABMS Data for Fraction $B^{KL}$ | | | |
|---|---|---|---|
| Pooled Fraction # | Original Tube #[a] | Weight | FABMS Peaks[b] |
| B-1 | 9-14 | 8.1 | |
| -2 | 15-17 | 4.3 | |
| -3 | 18-19 | 2.2 | 787[c], 769[c], 752[c] |
| -4 | 20-21 | 4.4 | 771 |
| -5 | 22-26 | 6.2 | 771 |
| -6 | 27-28 | 1.2 | 737, 753[c], 771 |
| -7 | 29-50 | 50.9 | 737 |
| -8 | 51-56 | 18.9 | 737 |
| -9 | 57-63 | 32.3 | 723 |
| -10 | 64-69 | 200.0 | 744 |

[a]18 mL/Tube.
[b]Observed ions (M + H)+.
[c]Unidentified peak.

Fraction B-7, containing mainly Compound 1, was further separated, first by normal phase and then by reversed-phase silica gel columns, to give pure Compound 1 (26.0 mg). Fraction B-9 was also separated and purified by a silica gel gravity column following by reversed-phase silica gel HPLC to give Compound 2 (4.1 mg).

Figure 3:
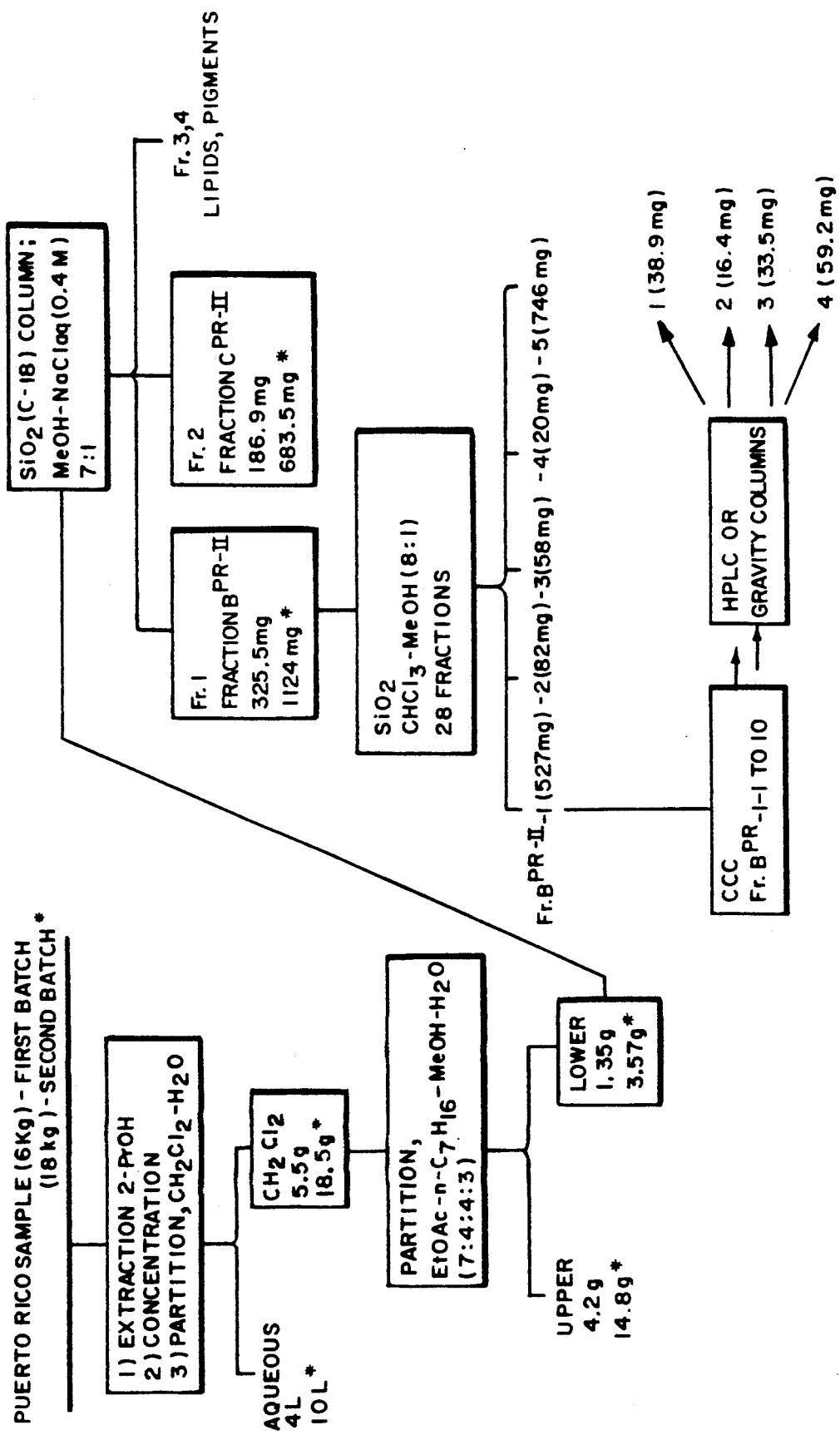

Ecteinascidins 736 (Compound 1), 722 (Compound 2), 729 (Compound 3), and 743 (Compound 4) were isolated by extraction of a tunicate sample (24 kg) collected in Puerto Rico in July 1990. This sample was extracted and processed by the procedure shown in FIG. 3, to give alkaloid-rich Fraction $B^{PR-II}$ (1.47 g), which was separated by a silica gel column into five fractions. The first fraction was further separated by CCC into 10 fractions (Fractions $B^{PR-II}$-1 to -10). The separation and FABMS data for each fraction are given in Table 2.

TABLE 2

| First CCC Separation and FABMS Data for Puerto Rico Sample | | | |
|---|---|---|---|
| Pooled Fraction # | Original Tube #[a] | Weight | FABMS Peaks[b] |
| $B^{PR}$-1-1 | 1-3 | 20.0 | 723, 737 |
| 2 | 4-5 | 47.1 | 737 |
| 3 | 6-8 | 41.4 | 723, 737 |
| 4 | 9-12 | 29.9 | 730, 744, 771, 802[c] |
| 5 | 13-23 | 164.6 | 744, 746, 730 |
| 6 | 24-28 | 63.2 | 730, 691[c] |
| 7 | 29-33 | 64.1 | 730, 841[c] |
| 8 | 34-36 | 47.5 | |
| 9 | 37-42 | 44.4 | |
| 10 | stationary phase | 10 | |

[a]9 mL/Tube.
[b]Observed ions (M + H)+.
[c]Unidentified peak.

The second fraction of the above CCC ($B^{PR}$-1-2), containing Compound 1 as the major component, was separated by silica gel gravity column to give Compound 1 (38.9 mg, $1.6 \times 10^{-4}$%). The next fraction ($B^{PR}$-1-3) contained Compound 2 and was separated and purified by a gravity silica gel column to give Compound 2 (16.4 mg. $7.0 \times 10^{-5}$%).

The largest Fraction $B^{PR}$-1-5, containing mostly Compound 4, some Compound 5 and a small amount of Compound 3, was separated by repeating reversed-phase HPLC to give pure Compound 4 (60 mg, $2.5 \times 10^{-4}$%), Compound 5 (13.4 mg, $5.4 \times 10^{-5}$%), and a mixture of Compounds 4 and 3 (6.7 mg). Fraction $B^{PR}$-1-6 contained Compound 3 as the major alkaloidal component, which was separated by reversed-phase HPLC to afford pure 3 (33.5 mg, $1.4 \times 10^{-4}$%).

Structure of Ecteinascidins 736 (Compound 1) and 722 (Compound 2)

Ecteinascidin 736 (Compound 1) had the following physical characteristics; $[\alpha]D^{24} -76°$ (c 0.53, CHCl$_3$)] showed "molecular" ions at m/z 753.2588 (M−H)− in negative ion and at 737.2655 (M+H−H$_2$O)+ in positive ion FABMS, respectively. These data agree best with the molecular formula C$_{40}$H$_{41}$N$_4$O$_9$S ($\Delta$0.6 mmu) and the dehydrated molecular formula, C$_{40}$H$_{41}$N$_4$O$_8$S ($\Delta$1.8 mmu), respectively. The minor component Et 722 (Compound 2); $[\alpha]D^{25} -40°$ (c 1.64, CHCl$_3$)] showed a molecular ion at m/z 739.2433 (C$_{39}$H$_{39}$N$_4$O$_9$S, $\Delta$−0.5 mmu, M−H, negative ion FABMS), and a dehydrated molecular ion at 723.2496 (C$_{39}$H$_{39}$N$_4$O$_8$S, $\Delta$−0.7 mmu, M+H−H$_2$O, positive ion FABMS). In the $^1$H and $^{13}$C NMR spectra for Et 722, disappearance of the signal for the N-12 methyl group (2.23 and 41.1 ppm in $^1$H and $^{13}$C NMR spectra, respectively) from spectra of Et 736 and upfield shifts for the adjacent carbons C-11 and C-13, indicated that Compound 2 was the 12-N methyl derivative of Compound 1.

A comparison of NMR data (Table 3) of Compounds 1 and 4, showed that the chemical shifts and coupling patterns of the protons observed between 2.3 and 5.3 ppm, and the $^{13}$C NMR chemical shifts for aliphatic carbons observed between 10 and 93 ppm are similar to each other. This similarity in NMR data suggested that the same bis(tetrahydroisoquinoline) A and B subunits are present in both compounds. This was supported by two-dimensional correlation NMR spectral data of Compound 1, including short and long range COSY (Bax, A., et al., *J. Magn. Reson.*, 1981, 42, 164), phase-sensitive COSY (Marion, D., et al., *Biochem. Biophys. Res. Commun.*, 1983, 113, 967–974), chemical shift correlation maps (CSCM) (Freeman, R., et al., *J. Chem. Soc. Chem. Commun.*, 1978, 684), and correlation by long range coupling (COLOC) (Kessler, H., et al., *J. Magn. Res.*, 1984, 57, 331–336). Scheme 1 (below) illustrates the correlations observed in those spectra which allowed assignment of all the protons and carbons on the subunits A and B in Compound 1, although some of the expected correlations were missing, presumably due to the broad peaks observed.

TABLE 3

$^1$H and $^{13}$C NMR Data of Et's 743 (4), 729 (3), 736 (1), and 722 (2) in 3:1 CD$_3$OD—CDCl$_3$ and Et 759B (6) in CD$_3$OD. Chemical Shift, δppm, and multiplicity, (J Hz)

| | 4 | | 3 | | 6 | | 1 | | 2 | |
|---|---|---|---|---|---|---|---|---|---|---|
| | $^{13}$C | $^1$H | $^{13}$C | $^1$H | $^{13}$C | $^1$H | $^{13}$C[a] | $^1$H | $^{13}$C | $^1$H |
| 1 | 56.3, d | 4.78, brs | 56.8, d | 4.69, br s | 57.1, d | 4.83 brs | 54.8, d | 4.71, br s | 56.7, d | 4.72, br s |
| 3 | 58.8, d | 3.72[b] | 57.1, d | 3.72 br d, (5.5) | 59.7, d | 3.85 brd | 57.8, d | 3.76, br s | 58.5, d | 3.53, d, (4.5) |
| 4 | 42.7, d | 4.58, br s | 42.5, d | 4.58, br s | missing | | 42.3, d | 4.58, br s | 43.1, d | 4.50, br s |
| 5 | 142.2, s | | 142.3, s | | 143.3, s | | 140.8, s | | 141.9, s[c] | |
| 6 | 113.9, s | | 114.0, s | | 113.9, s | | 112.6, s | | 113.4, s | |
| 7 | 146.5, s[c] | | 146.6, s[c] | | 147.53, s | | 145.4, s | | 146.8, s | |
| 8 | 141.9, s | | 141.5, s | | 142.4, s | | 140.5, s | | 142.1, s[c] | |
| 9 | 116.0, s | | 115.5, s | | 116.2, s | | 115.4, s | | 115.9, s | |
| 10 | 122.0, s | | 121.4, s | | 121.9, s | | 120.9, s | | 121.8, s | |
| 11 | 55.6, d | 4.40, br d, (3.5) | 47.8, d | 4.73, (5.0) | 55.8, d | 4.59, d, (4.5) | 54.5, d | 4.73, br s | 48.0, d | 44.44, d, (4.8) |
| 12 | 54.0, d | 3.52, br s | 47.2, d | 3.94, d, (10.0) | 53.7, d | 3.43, d, (10.0) | 52.6, d | 3.90, br d | 46.9, d | 3.57, br d, (9.0) |
| 13 | | | | | | | | 3.30[d] | | 3.15, d, (17.7) |
| 14 | 24.5, s | 2.91, 2H, br d, (4.5) | 25.1, t | 3.22, d, (18.0) 3.12, dd, (9.8, 18.0) | 25.2, d | 2.62, d, (18.0) 2.92, dd, (18.0, 9.0) | 23.2, t | 3.08, dd, (10.0, 19.0) | 27.9, t | 3.01, dd, (17.7, 9.3) |
| 15 | 120.9, d | 6.55, s | 121.2, d | 6.62, s | 122.0, s | 6.57, s | 120.3, d | 6.70, s | 121.0, d | 6.59, s |
| 16 | 131.2, s | | 130.6, s | | 131.9, s | | 130.3, s | | 131.4, s | |
| 17 | 145.1, s | | 144.9, s | | 146.3, s | | 143.0, s | | 144.4, s | |
| 18 | 149.8, s | | 148.6, s | | 150.1, s | | 148.2, s | | 148.2, s | |
| 19 | 119.2, s | | 120.2, s | | 119.3, s | | 118.5, s | | 124.3, s | |
| 20 | 131.5, s | | 132.7, s | | 131.9, s | | 130.9, s | | 132.2, s | |
| 21 | 92.1, d | 4.26, d, (3.0) | 90.1, d | 4.33, d, (3.0) | 92.4, d | 4.19, d, (2.5) | 91.5, d | 4.46, d, 2.4 | 91.1, d | 4.12, s |
| 22 | 61.2, s | 5.14, d, (11.0) 4.09, dd, (11.0, 2.0) | 51.5, s | 5.15, d, (11.0) 4.11, dd, 2.5, 11.0) | 62.6, s | 4.9, ov 4.30, dd, (11.5, 2.0) | 62.0, s | 5.20, dd, (12.5, 0.5) 4.18, dd, (12.5, 1.5) | 61.6, s | 5.17, dd, (11.1) 4.14, dd, (11.4, 1.2) |
| OCH$_2$O | 103.1, t | 6.07, d, (1.0) 5.98, d, (1.0) | 103.1, t | 6.09, d, (0.5) 6.00, d, (0.5) | 103.8, s | 6.15, d 6.05, s | 101.7, s | 6.26, d, (1.0) 6.07, d, (1.0) | 103.1, s | 6.21, d, (1.0) 6.04, d, (1.0) |
| 1' | 65.3, s | | 65.2, s | | 62.4, s | | 61.9, s | | 63.1, s | |
| 3' | 40.1, t | 3.13, dt, 4.0, (11.0) 2.77, ddd, (3.5, 5.5, 11.0) | 40.4, t | 3.12, m 2.77, m | 40.9, t | 3.04, dt, (5.0, 12.0) 2.85, dt, (12.0, 5.0) | 39.6, t | 2.90, dt, (11.5, 4.5) | 40.6, t | 3.30, m 2.86, m |
| 4' | 28.6, t | 2.60, ddd, (5.5, 10.5, 16.0) 2.42, ddd, (3.5, 3.5, 16.0) | 28.6, t | 2.60, ddd, (5.5, 10.5, 16.0) 2.42, ddd, (3.5, 3.5, 16.0) | 29.5, t | 2.43, dt, (4.5, 16.0) 2.60[d] | 20.9, t | 2.63, br s | 21.6, t | 2.61, 2H, m |
| 5' | 115.6, d | 6.38, s | 115.7, d | 6.39, s | 116.2, d | 6.29, brs | 116.9, d | 7.33, d, (8.0) | 118.8, d | 7.31, d, (7.8) |
| 6' | 146.4, s[c] | | 146.4, s[c] | | 147.0, s | | 117.7, d | 6.92, dt, (0.6, 8.0, 8.0) | 119.6, d | 6.91, dt, (0.9, 7.8, 7.8) |
| 7' | 146.4, s[c] | | 146.4, s[c] | | 147.0, s | | 120.7, d | 7.02, dt, (0.6, 8.0, 8.0) | 122.5, d | 7.00, dt, (0.9, 7.8, 7.8) |
| 8' | 111.3, d | 6.42, brs | 111.3, d | 6.41, brs | 111.3, d | 6.42, s | 111.7, d | 7.29, d, (8.0) | 111.9, d | 7.21, d, (7.8) |
| 9' | 125.4, s | | 125.2, s | | 125.2, s | | 135.6, s | | 137.4, s | |
| 10' | 128.8, s | | 129.0, s | | 129.9, s | | 126.6, s | | 127.3, s | |
| 11' | 173.1, s | | 173.2, s | | 173.2, s | | 171.2, s | | 172.5, s | |
| 12' | 43.1, t | 2.38, br d, (15.5) | 42.7, t | 2.40 2.07[c] | 69.6, t | 3.8[f] | 38.9, t | 2.78, d, (15.6) 2.15, br d, (15.3) | 39.9, t | 2.74, d, (15.0) 2.12, br d, (15.0) |
| 13' | | | | | | | | | 130.8, s | |
| 14' | | | | | | | | | 109.8, s | |
| 5 C=O | 169.8, s | | 169.8, s | | 170.9, s | | | | 170.7, s | |
| 5 OAc | 20.5, s | 2.29, s | 20.5, q | 2.30, s | 20.4, q | 2.24, s | 20.3, q | 2.28, s | 20.6, q | 2.27, s |
| 6 CH$_3$ | 9.9, q | 2.01, s | 9.8, q | 2.02, s | 10.0, q | 2.05, s | 9.4, q | 2.02, s | 9.7, q | 2.01, s |
| 16 CH$_3$ | 16.1, q | 2.28, s | 16.1, q | 2.29, s | 16.1, q | 2.27, s | 15.7, q | 2.37, s | 16.2, q | 2.32, s |
| 17 OCH$_3$ | 60.2, q | 3.72, s | 60.3, q | 3.71, s | 60.6, q | 3.76, s | 60.0, q | 3.76, s | 60.3, q | 3.72, s |
| 7 OCH$_3$ | 55.7, q | 3.58, s' | 55.6, q | 3.58, s | 55.9, q | 3.59, s | | | | |

TABLE 3-continued $^1$H and $^{13}$C NMR Data of Et's 743 (4), 729 (3), 736 (1), and 722 (2) in 3:1 CD$_3$OD—CDCl$_3$ and Et 759B (6) in CD$_3$OD.
Chemical Shift, δppm, and multiplicity, (J Hz)

| | 4 | | 3 | | 6 | | 1 | | 2 | |
|---|---|---|---|---|---|---|---|---|---|---|
| | $^{13}$C | $^1$H | $^{13}$C | $^1$H | $^{13}$C | $^1$H | $^{13}$C$^a$ | $^1$H | $^{13}$C | $^1$H |
| 12 NCH$_3$ | 41.1, q | 2.23, s | | | 38.9, q | 2.11, s | 40.9, q | 2.49, br s | | |

$^a$Proton assignments are made based on COSY and homonuclear decoupling experiments; carbon multiplicities were determined by APT and DEPT spectra. Carbons for 4 were assigned by analogy to those of 3.
$^b$7:1 CD$_3$OD—CDCl$_3$.
$^c$Signals overlap with methyl singlet.
$^d$Signals overlap with solvent peak.
$^e$Assignments are interchangeable.
$^f$Appeared only in HMQC spectra.

SCHEME 1 a. COSY, Long-range COSY, and Phase-sensitive COSY correlations.

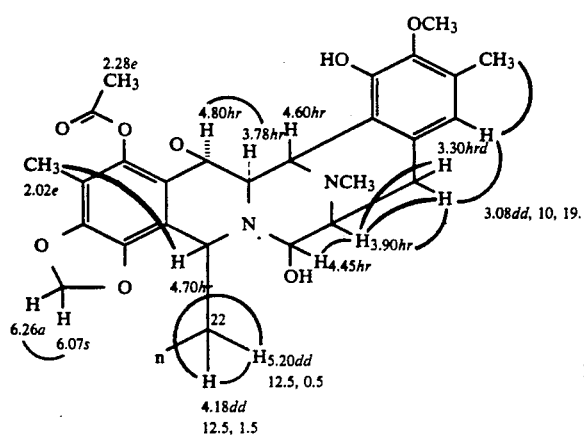

b. COLOC correlations

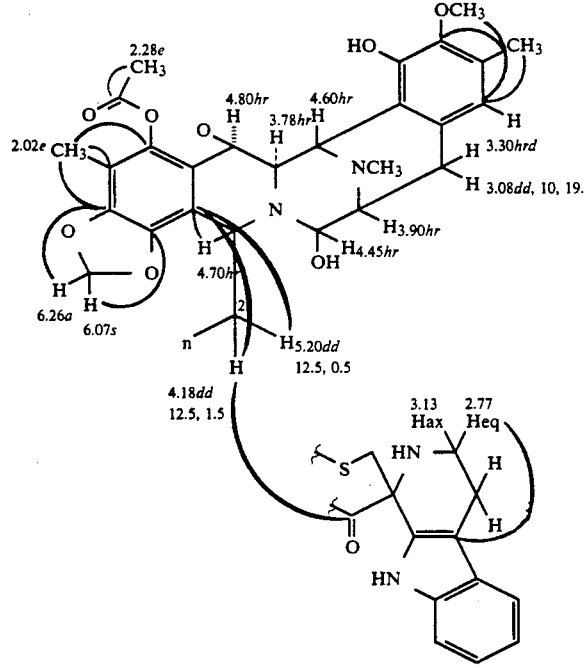

Identity of the subunits A and B in Compounds 1 and 4 was verified by comparison of HRFABMS data and FABMS/MS data between them. Important fragmentation ions observed in FABMS or FABMS/MS spectra of Compound 4 for the bis (tetrahydroisoquinoline) units A-B at m/z 523, 495, 477, 463, 218 and 204 were also observed in those of Compound 1 (see, Scheme 2, below). Molecular formulas of those ions were secured by HRFABMS analyses, which confirmed the composition of each peak (Table 4). In addition, FABMS/MS spectra on the key fragment ion at m/z 493, were contains the intact subunits A and B, in compounds 1 and 4, were essentially identical (FIG. 149), arguing bis(tetrahydroisoquinoline) subunits A and B in both compounds are the same.

TABLE 4

FABMS Data for Et 743 (4) and Et 736 (1)

| Observed Ion | | Formula | Fragment |
|---|---|---|---|
| 4 | 1 | | |
| 744.2648 | | $C_{39}H_{42}N_3O_{10}S$ | $(M + H - H_2O)$ |
| | 737.2655 | $C_{40}H_{41}N_4O_8$ | $(M + H - H_2O)$ |
| 523.2011 | 523.1960 | $C_{28}H_{31}N_2O_8$ | a + 2H |
| 495.2126 | 495.2126 | $C_{27}H_{31}N_2O_7$ | b + 2H |
| 493.1980 | 493.1980 | $C_{27}H_{29}N_2O_7$ | b |
| 477.1978 | 477.2024 | $C_{27}H_{29}N_2O_6$ | c |
| 463.1837 | 463.1862 | $C_{26}H_{27}N_2O_6$ | d |
| 218.1174 | 218.1180 | $C_{13}H_{16}NO_2$ | f |
| 204.1027 | 204.1025 | $C_{12}H_{14}NO_2$ | e − H |

SCHEME 2

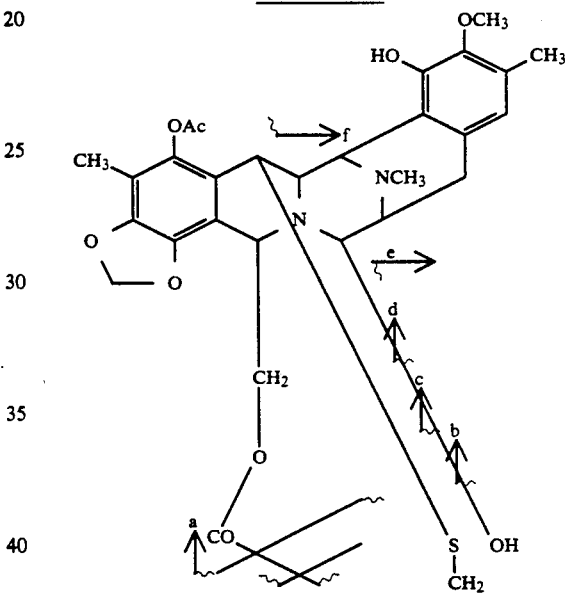

Addition of 5 ml (about 10 equiv.) of $CD_3OD$ to a $CDCl_3$ solution of Compound 1 gave a drastic downfield shift for the C-21 signal (from 81 to 90 ppm) in $^{13}C$ NMR spectra, due to the chemical exchange of OH at C-21 by $OCD_3$, just as in the case of Compound 4 (from 82 to 90 ppm). Similarly, treatment of Compound 1 with methanol at room temperature followed by evaporation of the solvent gave a mixture of unreacted Compound 1 and the 21-O-methyl derivative Compound 1a whose $^{13}C$ NMR spectrum showed the original C-21 signal at 82 ppm and a small "shifted" signal at 90 ppm. It should be noted that signals in the region 50–64 ppm in both experiments shifted upon treatment with methanol.

Negative ion FABMS spectra of Compound 1a gave a molecular ion at m/z 767.2761, which agreed with the molecular formula for a methanol adduct, $C_{41}H_{42}N_4O_9S$ (M−H, Δ0.1 mmu). It is noteworthy that the M−H (m/z 767) peak in Compound 1a appeared smaller than expected compared to the M−(m/z 768) peak due provably to electron transfer in the FAB condition. This series of experiments not only confirmed the existence of the C-21 carbinolamine functionality in Compound 1, but also demonstrated its facile reactivity to nucleophiles.

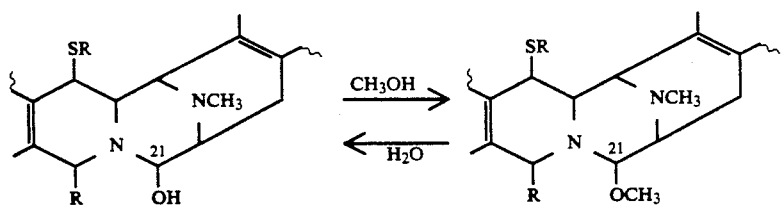

Subtraction of the bis(tetrahydroisoquinoline) unit A-B ($C_{27}H_{29}N_2O_7$) from the molecular formula of Compound 1 gives the formula $C_{13}H_{12}N_2OS$ for the rest of the molecule (subunit C'). The $^{13}C$ NMR signals for this subunit include one ester carbonyl carbon at 172.5 ppm and eight $sp^2$ carbons, leaving three rings for this subunit. An ortho disubstituted benzene ring was assigned to the subunit C' from the four aromatic signals at 7.33 (d, J=8.0), 699 (ddd, J=0.6, 8.0), 7.12 (ddd, J=0.6, 8.0), 7.29 (d, J=8.0) in the $^1H$ NMR spectrum of Compound 1, and this was expanded into a 2,2-dialkyl substituted indole by the near identify of the signals for C-5' through C-10' with those for the corresponding carbons of tetrahydronorharmane or related alkaloids containing β-carboline nuclei (see, Morales-Rios, M. S., et al., *Mag. Resn. Chem.*, 1987, 25, 377–395; and Shamma, M., et al., *Carbon*-13 *NMR Shift Assignments of Amines and Alkaloids;* Plenum: New York; 1979).

An [Ar-CH$_2$-CH$_2$-N<] system was identified from $^1H$ and $^{13}C$ NMR chemical shifts, along with the connectivities obtained from COSY and CSCM experiments (see, Scheme 3, below). The remaining carbons (C-1', C-11', C-12') of Compound 1 have chemical shifts close to those of C-1', C-11', C-12' in Compound 4, and they, with the sulfur atom, were assembled readily into the tetrahydro-β-carboline system (Scheme 3). Both $^1H$ and $^{13}C$ NMR data for Compound 1 for the subunit C' closely resemble those for the tetrahydro-β-carboline of debromoeudistomin L (Compound 54) (see, Nakagawa, M., et al., *J. Am. Chem. Soc.*, 1989, 111, 2721–2722). A COLOC correlation observed between equatorial H-3' (2.77 ppm) and C-14' (109 ppm) also supported the β-carboline system. HRFABMS data on fragment ions at m/z 216 and 243, which were seen in both FABMS and FABMS/MS spectra, verified this assignment (Scheme 3).

SCHEME 3

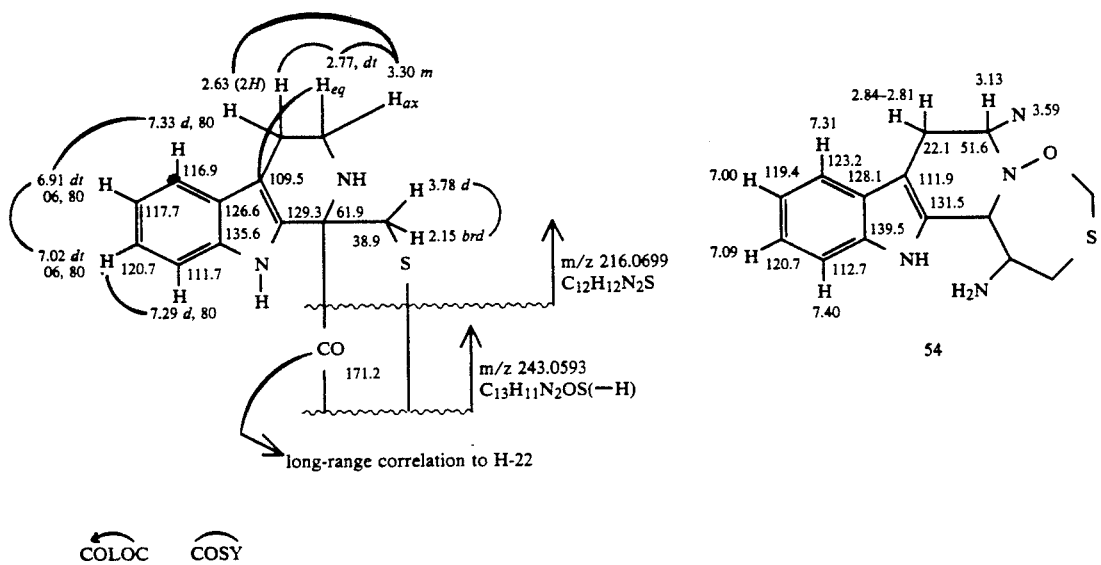

long-range correlation to H-22

COLOC   COSY

A long range COLOC correlation between C-11' and H-22, along with ester carbonyl absorption at 1753 cm$^{-1}$ in the IR (CCl$_4$) spectra (not shown), agreed with the ester linkage between C-11' and C-22. The molecular formula, $C_{40}H_{42}N_4O_9S$, requires 22 degrees of unsaturation, one or more than assigned thus far. The additional ring required is most consistent with $^{13}C$ NMR chemical shifts if it is formed between —S— and C-4 of the tetrahydroisoquinoline unit B as seen in the Et 743 series.

A possible conformation of ring f in the subunit C was proposed by $^1H$ NMR analysis. The coupling constant observed between H-3a and H-4a in all Et's is 10 to 12 Hz, indicating the dihedral angle of C-3'--H-3'a and C-4'--H4'a is about 180°, and thus in a trans-diaxial relationship to each other. The reset of the couplings equatorial - equatorial and axial-equatorial, are in the range 3.5 to 5 Hz in all Et's, suggesting ring in subunit C is in a half-chair conformation. A schematic drawings of ring f is given below, with NMR data for Compound 4 as an example.

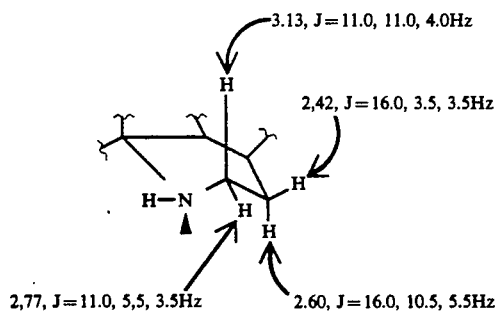

Structure of Ecteinascidin 759 B (Compound 6).

Although the structure of ecteinascidins 759 A (Compound 12) and 759 B (Compound 6) were tentatively assigned as N-oxide derivatives of Compound 4 based on their mass spectral data, the small quantities of pure samples have hampered an unambiguous structural determination. (See for example, Holt, T. G. Ph. D. Dissertation, University of Illinois at Urbana, 1986; Rinehart, K.L., et al., U.S. Ser. No. 872,189, filed Jun. 9, 1986; PCT Int. Appl. W08707610, Dec. 17, 1987; Chem. Abstr., 1988, 109, 811j; Rinehart, K.L., 30 th Ann Mtg. Am. Soc. Pharmacognosy, San Juan, P. R., Aug. 6-10, 1989; Rinehart, K.L., et al., J. Nat. Prod., 1990, 53, 771-792; Rinehart, K.L., et al., Topics in Pharmaceutical Sciences; Breamer, D.D.; Crommelin, D.J.A; and Midha, K.K., Eds; Amsterdam Medical Press B. V., Noorwiijk, the Netherlands, 1989; pp. 613-626; Rinehart, K.L., et al., J. Org. Chem., 1990, 55, 4512-4515; Rinehart, K.L., et al., Biological Mass Spectrometry; Burlingame, A.L. and McCloskey, J.A., Eds.; Elsevier, Amsterdam, 1990; pp. 233-257; Wright, A.E., et al., J. Org. Chem., 1990, 55, 4508-4512). Therefore, the structure determination of Compound 6 was carried out using a sample isolated from the Key Largo specimen. A comparison of TLC and mass spectral data of Compound 6 with those of Ecteinascidins 759 A and 759 B and mono-ocy Et 743, previously isolated or prepared by Holt (supra), showed that Et 759 B and Compound 6 were identical in both FABMS/MS and amino HPTLC data.

The molecular formula ($C_{39}H_{41}O_{11}S$) of Compound 6 was secured by HRFABMS (760.2550, $M+H-H_2O$, positive FABMS, and 776.2446, $M-H$, negative FABMS). A comparison of FABMS/MS data on m/z 760 for Compound 6 (see, Scheme 4, below) with those on m/z 744 for Et 743 (Compound 4) showed similar fragmentation patterns a-e for the subunits A and B, while the fragment ion for the subunit C shifted by 16 mass units (Scheme 4).

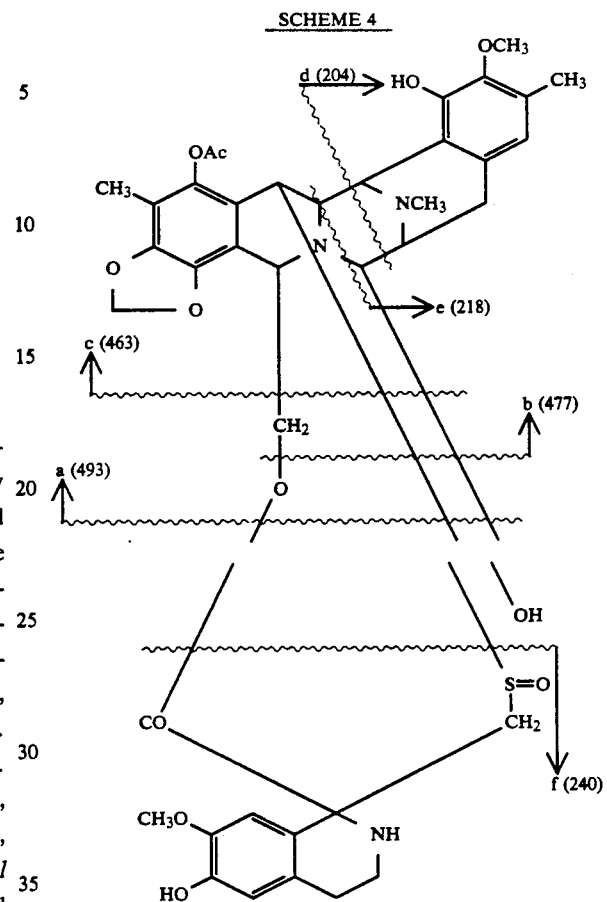

SCHEME 4

Also, the HRFAB and FABMS/MS spectra of Compounds 6 and of 4 on the fragment a (m/z 493) were essentially identical, indicating the extra oxygen must be located on the subunit C. The $^1H$ NMR spectrum of Compound 6 first appeared as a set of peaks, indicating the molecule exists as about a 1:1 mixture of conformers, which became a single spectrum during proton NMR measurement. The spectral patterns for the protons on A and B subunits in this $^1H$ NMR spectrum were similar to those of Compound 4. Although two signals, for H-4 and H-13', were not observed, probably due to peak broadening, COSY spectra of Compound 6 assignment of most of the signals, which were consistent with the identity of the subunits A and B to those in Compound 4, where subunits A and B were not oxidized. The chemical shifts and coupling patterns of the protons for the subunit C in Compound 6 were also very similar co those of Compound 4 (Table 4), suggesting the third tetrahydro- isoquinoline system was intact.

The $^{13}C$ NMR spectrum of Compound 6 (Table 3), which showed 38 signals, closely resembled that of Compound 4; most of the signals for Compound 6 corresponded to those of Compound 4 within 3 ppm. However, a methylene signal at 43.1 and a methyne signal at 42.7 ppm (C-12' and C-4) in Compound 4 disappeared in Compound 6, and a new methylene signal was observed at 69.6 ppm. This new methylene signal, assignable to C-12', has shifted downfield by 16 ppm in Compound 6, suggesting that the sulfur atom between C-4 and C-12' in Compound 6 is oxidized. IR spectra (KBr) of Compound 6 were not very indicative but showed a stronger absorption at 1257 cm$^{-1}$ compared to that of Compound 4 supporting the above argument.

Chemical Reactions of Ecteinascidins saframycin-type compounds. (See, Ishiguro, K., et al., *J. Biol. Chem.*, 1981, 256, 2162-2167).

Several chemical derivatizations of ecteinascidins were carried out (see, Scheme 5, below).

SCHEME 5

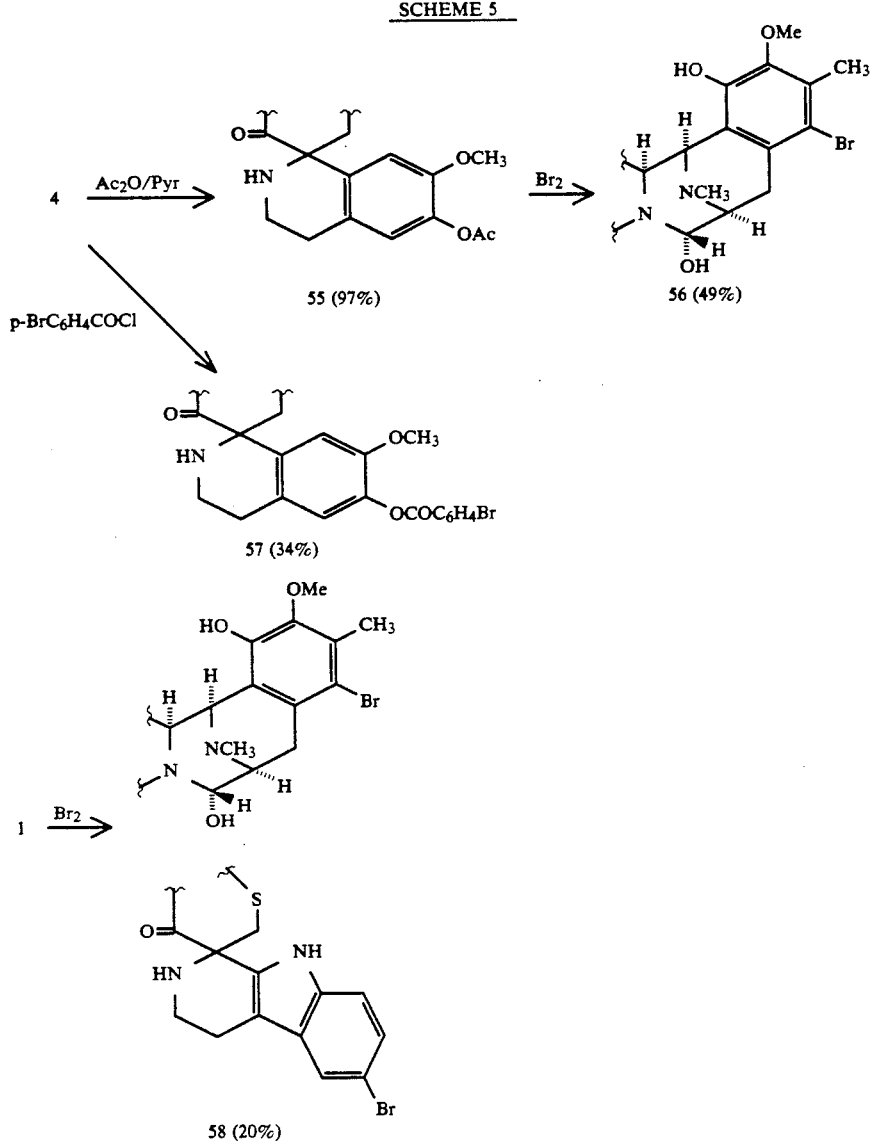

The most remarkable chemical property of ecteinascidins is the reactivity of the C-21 carbinolamine group. Because of the labile nature of the hydroxyl group at C-21, positive ion FAB mass spectra showed only a dehydrated species for all ecteinascidins which have the carbinolamine functional group, as seen in safracin B. Rapid chemical exchange of this hydroxyl group to a methoxyl group in methanol solution shown by $^{13}$C NMR and negative ion FABMS suggested that the C-21 substituent in these compounds can be replaced by some other nucleophile reversibly. In saframycin, it has been demonstrated by replacing the hydroxyl of saframycin S by cyanide under ambient conditions to give saframycin A, whereas the reverse reaction, treating saframycin S with aqueous sulfuric acid to yield saframycin A, required vigorous conditions. (See, Arai, T., et al., *J. Antiblot.*, 1980, 33, 951-960). This interesting characteristic of these molecules has been proposed to be the most important function for the biological activities of Reactions were mainly aimed to obtain a crystalline derivative which would be suitable for X-ray analysis. Monoand dibromo- derivatives of Et 743 (Compound 4) were previously prepared and X-ray analyses were carried out on them. However, the diffraction data were not satisfactory. Thus, the 6'-acetate of Et 3 (Compound 55) and its monobromo derivative (Compound 56) were prepared. Compound 56 was obtained as a crystal (large prism, from acetonitrile-water). X-ray analysis of the crystal was conducted, however, the diffraction data were not readily analyzed. A p-bromobenzoate derivative (Compound 57) was also obtained and attempts to crystallize it continue.

Reaction of Compound 1 with bromine or p-bromobenzoyl chloride were rather non-selective compared to those of Compound 4. A reaction with p-bromobenzoyl chloride gave a complex mixture which was difficult to purify. Reaction of Compound 1 with bromine gave the dibromo derivative Compound 58 in poor yield. Acylations of the hydroxyl group at C-18 in both Compounds 1 and 4 were less favored (slower reaction), implying steric hindrance of the hydroxyl group in tetrahydroisoquinoline subunit A.

Biological Activities of the Ecteinascidins

The ecteinascidins showed antimicrobial activity against Gram-positive bacteria and strong cytotoxicity against the L1210 murine leukemia cell line. Also Et's 722 (2) and 729 (3) showed potent in vivo activities against several tumor models in mice. These biological characteristics resemble those reported for saframycins and safracins and may be due to the carbinolainine group at C-21, as it has been proposed to be the most important functional group in the "activated form" of saframycin A. Thus, the mode of action of the Et's may involve covalent binding of the drug to DNA at C-21, which unpairs its template activity, as proposed for safracin A. The drastic loss of activity in Compound 5, which lacks the carbinolamine functional group, and the excellent in vivo activity of Compound 3 against Lewis carcinoma, which is sensitive only to alkylating agents, substantiates this assumption.

Cytotoxicity (L1210) and antitumor assays of the above ecteinascidins were carried out using standard procedures. For general information regarding the in vitro tumor cell line assay, see Hakala, M.T., et al., *Method in Cancer Research;* DeVita V.T. and Busch, H., Eds.; Academic Press: New York; Vol. XVI, 1987, p. 247. For general information regarding the in vivo assays, see Schabel, F.M. Jr., et al., *Method in Cancer Research;* DeVita, V.T. and Busch, H., Eds.; Academic Press: New York, Vol. XVII, 1979, pp. 26–29.

The in vitro L1210 murine leukemia assay showed that Compound 3 was the most potent of all, and that Compound 1 was the least active by an order of magnitude. Et 743 (Compound 3) and Et 722 (Compound 2) showed intermediate activity. These compounds, except for Compound 1, which showed the steepest curve, followed similar dose-response curves (see FIG. 9). Et 736 (Compound 1) and Et 722 (Compound 2) inhibited the growth of *M. luteus* with inhibition zones of about 12 mm at 450 and 300 ng/disc, respectively in the paper disc diffusion assay, while Et 743 (Compound 4) and Et 729 (Compound 3) gave the same size zone at 100 and 140 ng/disc, respectively.

In vivo activities of Compounds 2 and 3 against P388 lymphoma, B16 melanoma, and Lewis lung carcinoma in mice, showed that Compound 3 required a lower does than Compound 2, and was more active in the solid tumor assays (B16 and Lewis lung). Interestingly, Compound 2 showed a higher T/C in the leukemia model than did Compound 3. Compound 3 showed excellent activities not only against B-16 melanoma but also Lewis lung carcinoma in this assay (see, Table 5).

TABLE 5

In Vivo Antitumor Activities of 2 and 3[a]

| Tumor | Compound | Dose[b] μg/kg/inj | Day of death | Medium | T/C[c] | Alive (day) |
|---|---|---|---|---|---|---|
| P388 | 2 | 50.0 | 10, 13, 15, 15, 21 | 15.0 | 150 | 1 (21) |
| | | 25.0 | 13, 21 | >23 | >230 | 4 (21) |
| | | 12.5 | 14, 19, 20, 21, 22, 22 | 20.5 | 205 | 0 |
| | 3 | 50.0 | 7, 8, 10, 10, 10, 10 | 10.0 | 100 | 0 |
| | | 25.0 | 10, 13, 13, 13, 13, 13 | 13.0 | 130 | 0 |
| | | 12.5 | 12, 13, 17, 21 | 19.0 | 190 | 2 (21) |
| | 5FU[d] | 20.0 | 23, 23 | >23 | >230 | 4 (23) |
| | | 10.0 | 19, 19, 19, 21, 22, 22 | 20.0 | 200 | 0 |
| | 2 | 50.0 | 32, 32, 33, 34, 34, 34, 34, 35, 36 | 34.0 | 200 | 0 |
| | | 25.0 | 28, 30, 30, 30, 31, 32, 24, 24, 25, 25 | 31.5 | 185 | 0 |
| | | 12.5 | 17, 18, 23, 23, 26, 27, 29, 30, 30 | 26.5 | 156 | 0 |
| | 3 | 50.0 | 10, 11, 12, 12, 12, 14, 35, 36, 41, 42 | 13.0 | 76 | 0 |
| | | 25.0 | 34, 34, 35, 36, 41 | >42 | 253 | 5 (42) |
| | | 12.5 | 28, 30, 30, 31, 32, 35, 35, 35, 36, 37 | 33.5 | 197 | 0 |
| | Cis[e] | 1000.0 | 24, 27, 27, 29, 30, 30, 30, 32, 32, 33 | 30.0 | 176 | 0 |
| | | 500.0 | 22, 22, 23, 26, 26, 26, 27, 29, 30, 31 | 26.0 | 153 | 0 |

| Tumor | Compound | Dose[b] | Mean body wt. change (g. day 1-5) | Median tumor vol. on day 14 (mm³) | T/C[f] | NP/14[g] |
|---|---|---|---|---|---|---|
| Lewis lung | 2 | 50.0 | −0.5 | 395 | 0.29 | 0 |
| | | 25.0 | 1.0 | 908 | 0.66 | 0 |
| | | 12.5 | 1.9 | 1204 | 0.88 | 0 |
| | 3 | 25 | −1.8 | 0 | 0.00 | 7 |
| | | 12.5 | −0.2 | 0 | 0.00 | 7 |
| | | 6.25 | −0.1 | 173 | 0.13 | 3 |
| | Cyc[h] | 50000.0 | −2.7 | 0 | 0.00 | 10 |
| | | 25000.0 | −1.0 | 31 | 0.02 | 5 |

[a]Testing carried out at A. D. Little.
[b]Schedule once a day for nine consecutive days.
[c]Treated/control × 100(%); >125% is significant activity.
[d]5-Fluorouracil.
[e]Cisplatin.
[f]Treated/control; <0.40 is considered as significant activity.
[g]Nonpalpable tumors on day 14.
[h]Cyclophosphamide.

In Vitro L1210 Activities of Compounds 1–4.

Effects of the various Et's cell-mediated immune response was also determined. Spleen cells taken from Balb/c mouse were stimulated by concanavalin A, a T-cell specific mitogen in mice (see, Dwyer, J.M., et al., *Clin, Ex p. Immunol.*, 1981, 46, 237–249), then treated with each of the Et's. The antiproliferative activity was measured by counting incorporation of [³H]thymidine into the cells. Cell viability of non-stimulated cells (indicating general cytotoxicity) was assessed by MTT dye reduction. (see, Mosmann, T.J., *Immunol, Methods,* 1983, 65, 55). All tested compounds (1–4) showed strong antiproliferative activity against the concanavalin A-stimulated spleen cells at $IC_{50}$'s of 2–4 ng/ml in which more than 90% of the cells were viable. These results are shown in Table 6.

TABLE 6

Antiproliferative and Cytotoxic Potencies of Ecteinascidins[a]

| Compound | Antiproliferation[b] $IC_{50}$ (ng/mL) | % Viable cells at $IC_{50}$ | Cytotoxicity[c] $ED_{50}$ (ng/mL) | $ED_{50}/IC_{50}$[d] |
|---|---|---|---|---|
| Et 736 (1) | 3.64 ± 0.40 | 97 ± 2 | 38.4 ± 4.6 | 11.18 ± 4.3 |
| Et 722 (2) | 3.52 ± 0.23 | 91 ± 4 | 324.8 ± 8.6 | 6.78 ± 1.9 |
| Et 729 (3) | 1.87 ± 0.08 | 88 ± 7 | 15.3 ± 4.6 | 7.93 ± 2.2 |
| Et 743 (4) | 2.70 ± 0.70 | 89 ± 6 | 17.7 ± 4.3 | 7.46 ± 2.3 |

[a]Balb/c mouse spleen cells cultured for 72 h in RPMI 1640 + 10% FCS.
[b]Proliferation of concanavalin A-stimulated cells assessed by [$^3$H] thynudine incorporation.
[c]Viability of non-stimulated cells assessed by MTT dye reduction.
[d]$ED_{50}$ Cytotoxicity/$IC_{50}$ anti-proliferation.

Although the Et's seem to have the same principle mode of action as safracin A and safracin B as antitumor agents, the cytotoxicities of Compounds 2 and 3 are 10 and 50 times stronger than that of safracin A, while in vivo testing of Compound 2 requires a thirty times smaller, and that of Compound 3 a fifteen times smaller dose level for similar efficacy. This difference in potency can presumably be attributed to the molecular shape of the drug which may fit into a DNA groove more selectively than saframycins or safracins. In the ecteinascidins, an N-12 methyl group changes the bioactivities substantially. Also, subunit C seems to contribute to the selectivity of in vivo systems since Compound 2 was more active than Compound 3 against leukemia but Compound 3 showed much higher potency against solid tumor models than Compound 2. These interesting selectivities of in vivo tumor models demonstrate the importance of the structure of subunit C.

The ecteinascidins are also shown to suppress cell-mediated response of mouse spleen cells in vitro. An anti-mitogenesis assay was carried out using concanavalin A-stimulated mouse spleen cells which reveal the antiproliferative action of the compounds against activated T-cells. All Et's tested (Compounds 1–4) showed strong antiproliferative activity against activated T-cells.

All Et's tested (Compounds 1–4) showed strong antiproliferative activity against concanavalin A-stimulated murine spleen cells at $IC_{50}$'s of 3.6, 3.5, 1.9 and 2.7 ng/ml, respectively. At these concentrations cell viabilities are 97, 91, 88 and 89%, respectively. The Et 743 series were more active than the Et 736 series, but cell viability at $IC_{50}$ in the Et 736 series was higher than that of the Et 743 series. The relative potencies ($ED_{50}$ cytotoxicity/$IC_{50}$ antiproliferative activity) was highest (11.2) in Et 736 (Compound 1), while others showed values around 7 to 8, indicating Compound 1 has more selective antiproliferative activity than other Et's.

This potent antiproliferative activity against concanavalin A-stimulated murine spleen cells is comparable to that of the clinically important immunosuppressive agent, Cyclosporin A, with $IC_{50}$ at 3 ng/ml in a similar assay system. (See, Nakamura, A., et al., *J. Antibiot.,* 1986, 39, 1148–1154; and Tsuji, R.F., et al., *J. Antibiot.,* 1990, 43, 1293–1301). This immunosuppressive activity of the Et's warrant further investigation, including antiproliferative activity against mitogen stimulated B-cells, inhibitory effects on the mixed lymphocyte reaction, and an in vivo graft-vs-host assay to fully evaluate the immunosuppressive activity of ecteinascidins.

Other important bioactivities of the Et's are shown in the following tables. In Table 7, the anti-HSV (I) activity is illustrated.

TABLE 7

Inhibition of Herpes simplex virus, Type 1 by selected Ecteinascidins[a]

| Dose (ng/2 × $10^5$ cells) | Et 729 | Et 743[c] | Et 745 | Monoxy Et 743 |
|---|---|---|---|---|
| 1000 | | +++ | | |
| 500 | +++ | + | | ++ |
| 200 | +++ | − | | − |
| 100 | +++ | | | |
| 50 | +++ | | | |
| 20 | ++ | +++ | | |
| 10 | − | +++ | | |
| 5 | | +++ | | |
| 2 | | +++ | | |
| 1 | | ++ | | |
| 0.5 | | + | | |
| 0.2 | | − | | |

[a]HSV-1 virus grown in monkey kidney (CV-1) cells; no zone of cytotoxicity to CV-1 cells was observed for any of these pure ecteinascidin samples; antiviral activity is reported as: +++, no viral plaques visible by microscope; ++, viral plaques observed without microscope only at the extreme edge of the test well; +, plaques observed throughout the well at reduced size and number; −, no antiviral effect.
[b]Stored and applied in methanol, unless otherwise noted.
[c]Stored and applied in isopropyl alcohol-water (1:1).

TABLE 8

Activity in vivo of Ecteinascidin 729

| Dose µg/Kg/ml | P388 lymphocyclic leukemia | | B16 melanoma | | Lewis lung carcinoma | |
|---|---|---|---|---|---|---|
| | T/C[a] | Survivors (day) | T/C[a] | Survivors (day) | T/C[b] | Mean tumor volume (ram$^3$) |
| Control | 100 | 0(12) | 100 | 0 | 1.00 | 1512 |
| Et 729 | | | | | | |
| 25.0 | 130 | 0(13) | 76 | 0(42) | 0.00 | 2 |
| 12.5 | 190 | 2(21) | 253 | 5/10(42) | 0.04 | 57 |
| 6.25 | NT | NT | 197 | 0(37) | 0.14 | 216 |

Significant activity:
[a]T/C ≥ 125;
[b]T/C ≤ 40.

TABLE 9

TUMOR GROWTH INHIBITION - Day 14

Tumor: 816  Species: Mouse
Generation: 77801  Strain: BDF1
Tissue: SOLID TUMOR  Male
Level: 1:10 BREI  Source: Charles River Kingston
Site: 0.5 ml, Sc.  DOB:

| Test # | Compound | Dose µg/kg/Inj | Schedule & Route | Mean Body Wt Change (grams) Day 1–5 | N.P. D-14 | Median Tumor Vol. (mm 3) | T/C | Mean Tumor Vol. (mm 3) | ST DEV | T/C | T |
|---|---|---|---|---|---|---|---|---|---|---|---|
| | ET 729 | 25.00 | 001-9, 1P | −1.8 | 7 | 0 | 0.00 | 2* | 8 | 0.00 | 23,625 |

TABLE 9-continued

| TUMOR GROWTH INHIBITION - Day 14 | | | | | | | | | |
|---|---|---|---|---|---|---|---|---|---|
| 12.50 | −0.2 | 7 | 0 | 0.00 | 57* | 120 | 0.04 | 20,821 |
| 6.25 | −0.2 | 3 | 173 | 0.13 | 216* | 223 | 0.14 | 15,883 |

N.P. = # of Non-palpable Tumors on Day 14
*Significant Activity: T/C < = 0.40 and p = < 0.01 By t Test

TABLE 10

Interim Results: Day 42
ANTI-TUMOR ACTIVITY VS. B16 MELANOMA

Tumor: B16   Species: Mouse
Generation:   Strain: 8DF1
Tissue: BREI   Sex: Male
Level: 1:10; 0.5 cc   Source: Charles River Kingston

| Test # | Compound | Dose ug/kg/inj | Schedule & Route | Change (gm) Day 5 | Day of Death | Survival Time | % T/C | Survival Time | % T/C | Day 24 |
|---|---|---|---|---|---|---|---|---|---|---|
| 13 | ET 729 | 25.00 | OD1-9, 1P | −1.6 | 10 11 12 12 12 14 35 36 41 42 | 22.5 | 129 | 13.0 | 76 | 0 |
| 14 | | 12.50 | | 0.0 | 34 34 35 36 41 45 47 47 48 52 | 41.9 | 241* | 43.0 | 283 | 5 |
| 15 | | 8.25 | | −0.2 | 28 30 30 31 32 35 35 35 35 37 | 32.8 | 189* | 33.5 | 197 | 0 |

B16 (0.5 ml, 1:10 brei) implanted ip into male BDF1 mice on day 0, compounds dissolved or suspended in sterile 0.9% NaCl solution (plus minimal amounts of ethanol and Tween-80 as needed) and administered ip days 1-9 in a volume of 0.5 ml/mouse. Mice were weighed days 1 and 5 and deaths were recorded daily.
*Significant activity: T/C > = 125%

TABLE 11

Interim Results: Day 23
ANTI-TUMOR ACTIVITY VS. P388 LYMPHOCYTIC LEUKEMIA

Tumor: P388   Species: Mouse
Generation: 77801   Strain: 8DF1
Tissue: SOLID TUMOR   Male
Level: 1:10 BREI   Source: Charles River Kingston
Site: 0.5 ml, Sc.   DOB:

| Test # | Compound | Dose ug/kg/inj | Schedule & Route | Body Wt. Change (gm) Day 5 | Day of Death | Mean Survival Time | % T/C | Median Survival Time | % T/C | Alive Day 23 |
|---|---|---|---|---|---|---|---|---|---|---|
| 13 | ET 729 | 50.00 | OD1-9, 1P | −2.5 | 7 8 10 10 10 10 | 9.2 | 90 | 10.0 | 100 | 0 |
| 14 | | 25.00 | | −0.2 | 10 13 13 13 13 13 | 12.5 | 123 | 13.0 | 130 | 0 |
| 15 | | 12.50 | | 0.1 | 12 13 17 21 | * | | 19.0 | 190 | 2 |

$10^{-6}$ P388 cells implanted ip into male CD2F1 mice on day 0. Compounds dissolved or suspended in sterile 0.9% NaCl solution (plus minimal amounts of ethanol and Tween-80 as needed) and administered ip days 1-9 in a volume of 0.5 ml/mouse. Mice were weighed days 1 and 5 and deaths were recorded daily.
*Significant activity: T/C > = 125%

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE 1

Ecteinascidin 736 (Compound 1)

A frozen sample of tunicate (19 kg) collected on Key Largo Fla., in August, 1988 was defrosted and gently squeezed to remove water. Solid tissue was soaked in 2-propanol (3×3.8 L). Aqueous alcohol extracts were combined and evaporated in vacuo to give an aqueous emulsion which was extracted completely with dichloromethane (3.8 L). The organic layer was concentrated in vacuo to give an oil (20.2 g). The oil was then partitioned between the upper and lower layers of heptane-dichloromethaneacetonitrile (50:15:35) to give a bioactive oil (5.76 g) from the lower layer. Solvent partition of the active oil between lower and upper layers of heptane-ethyl acetate-methanol-water (4:7:4:3, 1 L) yielded bioactive Fraction $A^{KL}$ from the lower layer (800 mg; 10 mm at 20 μu/disc, M. luteus).

The upper layer was essentially inactive (8 mm at 200 μg). The alkaloidal content of Fraction $A^{KL}$ was analyzed by FABMS. Fraction $A^{KL}$ was further separated by a reversed-phase silica gel gravity column into four fractions with methanol-aqueous sodium chloride (0.4M) (7:1). Fractions 1 (350 mg) and 2 (202 mg), designated as Fraction $B^{KL}$ and Fraction $C^{KL}$, respectively, were subjected to further separation. Fraction $B^{KL}$ (333 mg) was separated By CCC with ethyl acetate- benzene- cyclohexane- inethanol- water (3:4:4:4:3), using the upper phase as the mobile phase, into 69 fractions (18 ml/fraction, 1.8 ml/min.). Each fraction was monitored by silica gel TLC (methanol-chloroform, 8:1) and combined into 10 fractions (Fraction B-1 to -10, Table 1). Fraction B-7 (50.9 mg) from this separation was passed through a silica gel (treated with ammonia gas) column with chloroform-methanol (12:1). The first fraction (30.4 mg) was purified by HPLC (C-18) with acetonitrile- methanol-0.25M aqueous sodium chloride (5:7:3) to give Compound 1 (light brown amorphous solid, 25 mg, $1.3 \times 10^{-4}$%). A part (2 mg) of the solid was recrystallized from acetonitrile- water to give pure Compound 1.

Figure 4:
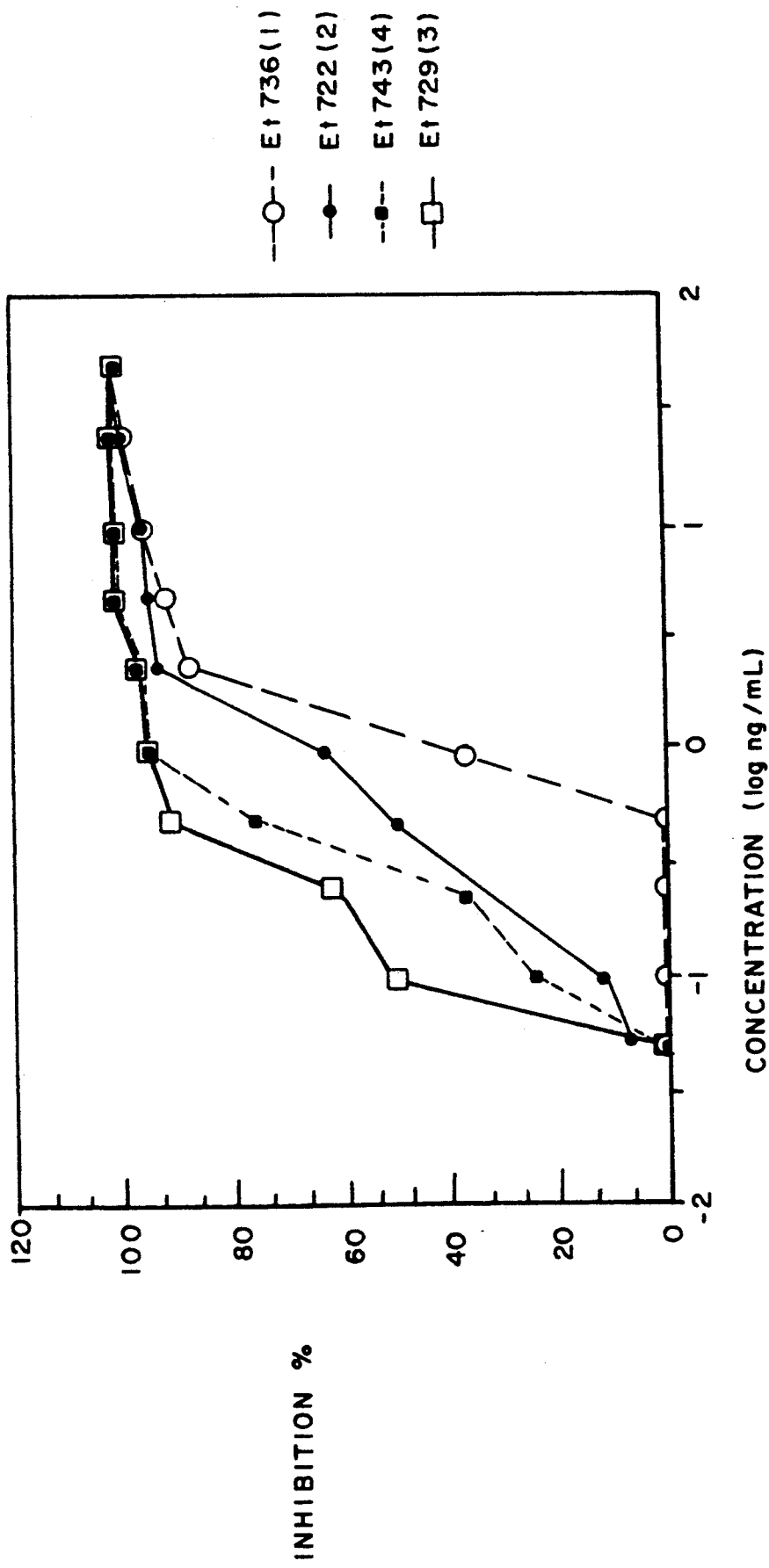
FIG. 4 illustrates the activity of several Et's in vitro against L1210 murine leukemia cells.

Ecteinascidin 736 (Compound 1) had the following characteristics: fine needles, m.p. 140°-150° C. dec.; $[\alpha]D^{24} - 76°$ (c 0.53, CHCl$_3$); IR (CCl$_4$) 3530, 3480 (NH, OH), 2928, 1768 (C=O), 1753 (C=O), 1196, 1153, 1089 cm$^{-1}$; IR (film) 3350, 3200 (NH, OH), 2928, 1753 (C=O), 1440, 1250, 1200, 1088 cm$^{-1}$ (FIG. 152); UV (MeOH) $\lambda_{max}$ 292 (log ε 4.97), 283 (4.09), 221 (sh. 4.65), 2.07 (4.77) nm; NMR data [Table 3 for assignments; $^1$H, $^{13}$C attached proton test (APT); COSY, Long-range COSY, Phase-sensitive COSY, CSCM and COLOC see FIGS. 145a, 145b, 146, 147, and 148, respectively]; FABMS m/z 737 (M+H−H$_2$O+), 495, 493, 463, 218, 204 (positive ion), m/z 753 (M−H−, negative ion) (FIG. 4); FABMS/MS [FIG. 164a (on m/z 737) and FIG. 149c (on m/z 493)]. Anal. Calcd. for C$_{40}$H$_{41}$N$_4$O$_9$S: 753.2595 (M−H). Found 753.2588 (M−H) (negative ion HRFABMS). Anal. Calcd. for C$_{40}$H$_{41}$N$_4$O$_8$S: 737.2637 (M+H−H$_2$O). Found 737.2655 (M+H−H$_2$O) (positive ion HRFABMS).

EXAMPLE 2

Ecteinascidin 722 (Compound 2)

Fraction B-9 (32.2 mg) of the above CCC separation was separated by a silica gel (treated with ammonia gas) column with chloroform-methanol (8:1). The first fraction from chromatography was purified by HPLC with acetonitrile- methanol- 0.25M aqueous sodium chloride (5:7:3) to give light brown amorphous, solid 2 (4 mg, 2.1×10$^5$%): m.p. 160°-164° C.; [α]D$^{24}$−40° (c 1.64, CHCl$_3$); IR (film) 3292 (NH, OH), 2930, 1753 (C=O), 1440, 1238, 1200, 1086 cm$^{-1}$ (FIG. 165); UV (MEOH) λ$_{max}$ 292 (log ε4.04), 283 (4.11), 276 (4.04), 221 (broad sh. 4.66), 207 (4.75) run (FIG. 162b) ; NMR data [Table XXIX for assignments; $^1$H, $^{13}$C (proton noise decoupled and APT), COSY, see FIGS. 144b, 166, and 167, respectively]; FABMS m/z 723 (M+H−H$_2$O, 204 (positive ion), m/z 739 (M−H−, negative ion) (FIG. 5); FABMS/MS on m/z 723 (FIG. 164b). Anal. Calc. for C$_{39}$H$_{39}$N$_4$O$_9$S; 739.2428 (M−H). Found 739.2433 (M−H) (negative ion HRFABMS). Anal. Calcd. for C$_{39}$H$_{39}$N$_4$O$_8$S: 723.2489 (M+H−H$_2$O). Found 723.2496 (M+H−H$_2$O) (positive ion HRFABMS).

Fraction B-10 (200 mg), the most polar fraction from the CCC separation, was further separated into five fractions by another CCC with chloroform-inethanol-water (4:4:3), using the lower layer as mobile phase (flow rate 1.8 ml/min., 18 ml/fr.).

EXAMPLE 3

Ecteinascidin 759B (Compound 6)

Fraction B-10-1 of the above described CCC separation was passed through a silica (ammonia gas treated) column with chloroform-methanol (10:1) to give a mixture of ecteinascidins (30.0 mg) which was separated by HPLC (amino) with chloroform- methanol-ethyl acetate (8:2:1) into three fractions. The first fraction was a mixture of Compounds 4 and 5 (13.4 mg). The second and third fractions, containing Compound 6, were combined and purified by HPLC (C-18) with methanol-aqueous sodium chloride (0.08M) (9:2) to give Compound 6 (3.54 mg; 8 mm at 160 ng/disc. *M. luteus*): m.p. 155° C., dec.; [α]D$^{24}$−184° (c 0.354, CHCl$_3$); IR (CCl$_4$) 3550, 1750, 1510, 1460, 1370, 1240, 1205, 1110, 1000 cm$^{-1}$ (FIG. 159); UV (MeOH) λ$_{max}$ 292 (log ε 4.05), 283 (4.11), 276 (4.04), 218 (4.66), 207 (4.63) nm (FIG. 162e); NMR data [Table 3 for assignments based on COSY data and comparison with those of Compound 4; for $^1$H, $^{13}$C (proton-noise decoupled, APT), COSY;

FABMS m/z 760 [(M+H−H$_2$O+), positive ion], m/z 776 [(M−H−), negative ion]; Anal. Calcd. for C$_{39}$H$_{42}$N$_3$O$_{12}$S: 776.2489 (M−H). Found 776.2446 (M−H) (negative ion HRFABMS). Anal. Calcd. for C$_{39}$H$_{42}$N$_3$O$_{11}$S: 760.2540 (M+H−H$_2$O). Found 760.2550 (M+H−H$_2$O) (positive ion HRFABMS)

EXAMPLE 4

Tryptamine Hydrochloride (Compound 53)

Fraction B-10-5 of the above described CCC was separated on a silica gel (50 g) column into 11 fractions with chloroform-methanol-water (15:10:2). Recrystallization of Fraction 7 (6.4 mg) gave 53 from chloroform-methanol (8:1): m.p. 230° C., dec. (lit.[50] 248° C.); $^1$H NMR (500 MHz, CD$_3$OD) 7.57 (1H, d, J=7.5), 7.36 (1H, d, J=8.5), 7.18 (1H, s), 7.11 (t, J=8.0), 7.03 (1H, t, J=8.0), 3.23 (2H, t, J=7.0), 3.13 (2H, t, J=7.0) (FIG. 168a); −C NMR (500 MHz, CD$_3$OD) 138.36 (s), 128.18 (s), 124.33 (d), 122.74 (d), 120.03 (d), 118.89 (d), 112.55 (d), 110.26 (s), 41.29 (t), 24.35 (t) (FIG. 168b).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A pharmaceutical composition comprising one or more ecteinascidin species selected from the group consisting of Et 736, Et 722, Et 743, Et 729, Et 745, Et 759(a), Et 770 and Et 729, in combination with a pharmaceutically acceptable carrier, diluent or excipient.

2. The pharmaceutical composition of claim 1, wherein the ecteinascidin (Et) is Et 736.

3. The pharmaceutical composition of claim 1, wherein the ecteinascidin (Et) is Et 722.

4. The pharmaceutical composition of claim 1, wherein the ecteinascidin (Et) is Et 743.

5. The pharmaceutical composition of claim 1, wherein the ecteinascidin (Et) is Et 729.

6. The pharmaceutical composition of claim 1, wherein the ecteinascidin (Et) is Et 745.

7. The pharmaceutical composition of claim 1, wherein the ecteinascidin (Et) is Et 759(a).

8. The pharmaceutical composition of claim 1, wherein the ecteinascidin (Et) is Et 770.

9. The pharmaceutical composition of claim 1, wherein the ecteinascidin (Et) is Et 729.

10. A method of treating herpes simplex virus (Type I) infections in mammals comprising administering to a mammal in need of such treatment, an anti-HSV-I effective dosage of a pharmaceutical composition comprising an ecteinascidin (Et) selected from the group consisting of Et 736, Et 722, Et 743, Et 729, Et 745, Et 759(a), Et 770, Et 729, or mixtures thereof, in a suitable carrier or diluent.

* * * * *

UNITED STATES PATENT AND TRADEMARK OFFICE
CERTIFICATE OF CORRECTION

PATENT NO. : 5,256,663
DATED : October 26, 1993
INVENTOR(S) : Kenneth Rinehart, Ryuichi Sakai and Tom G. Holt It is certified that error appears in the above-indentified patent and that said Letters Patent is hereby corrected as shown below:

On the title page, item [75], change "Sakai Ryuichi" to --Ryuichi Sakai--.

Column 1, line 6, insert the following:

--STATEMENT OF GOVERNMENT SUPPORT

Support for this invention was received from the National Institute of Allergy and Infectious Diseases under Grant No. Al 04769 and the National Institute of General Medical Sciences under Grant No. GM 27029. Thus the government of the United States of America has certain rights in this invention.--

Signed and Sealed this

Twenty-first Day of June, 1994

Attest:

BRUCE LEHMAN

Attesting Officer    Commissioner of Patents and Trademarks